US008828910B2

(12) United States Patent
Aksela et al.

(10) Patent No.: US 8,828,910 B2
(45) Date of Patent: Sep. 9, 2014

(54) PROCESS FOR THE PREPARATION OF PEROXY ACIDS

(75) Inventors: Reijo Aksela, Espoo (FI); Ilkka Renvall, Espoo (FI)

(73) Assignee: Kemira Oyj, Helsinki (FI)

( * ) Notice: Subject to any disclaimer, the term of this patent is extended or adjusted under 35 U.S.C. 154(b) by 1002 days.

(21) Appl. No.: 12/066,686

(22) PCT Filed: Sep. 13, 2006

(86) PCT No.: PCT/FI2006/000303
§ 371 (c)(1),
(2), (4) Date: Sep. 3, 2008

(87) PCT Pub. No.: WO2007/031596
PCT Pub. Date: Mar. 22, 2007

(65) Prior Publication Data
US 2009/0221704 A1    Sep. 3, 2009

(30) Foreign Application Priority Data
Sep. 13, 2005  (FI) ..................................... 20050913

(51) Int. Cl.
| | | |
|---|---|---|
| A01N 31/02 | (2006.01) | |
| A01N 37/02 | (2006.01) | |
| C07C 409/30 | (2006.01) | |
| C07C 409/24 | (2006.01) | |
| C07C 409/26 | (2006.01) | |
| A01N 37/16 | (2006.01) | |

(52) U.S. Cl.
CPC .............. *C07C 409/24* (2013.01); *A01N 37/02* (2013.01); *C07C 409/30* (2013.01); *C07C 409/26* (2013.01); *A01N 37/16* (2013.01)
USPC ........................................................ 504/160

(58) Field of Classification Search
CPC ..................................................... A01N 31/02
USPC ........................................................ 504/160
See application file for complete search history.

(56) References Cited

U.S. PATENT DOCUMENTS

| | | | | |
|---|---|---|---|---|
| 4,304,762 | A | * | 12/1981 | Leigh .............................. 423/272 |
| 5,200,189 | A | | 4/1993 | Oakes et al. |
| 6,096,226 | A | | 8/2000 | Fuchs et al. |
| 6,139,756 | A | | 10/2000 | Fuchs et al. |
| 6,211,237 | B1 | | 4/2001 | Huss et al. |
| 6,284,793 | B1 | | 9/2001 | Fuchs et al. |
| 2004/0035537 | A1 | | 2/2004 | Delmas et al. |
| 2005/0072743 | A1 | | 4/2005 | Schneider et al. |

FOREIGN PATENT DOCUMENTS

| | | |
|---|---|---|
| EP | 0231632 A2 | 8/1987 |
| WO | 9420424 | 9/1994 |
| WO | 2005045132 A1 | 5/2005 |

OTHER PUBLICATIONS

Written Opinion of the International Searching Authority; International Application No. PCT/FI2006/000303; International Filing Date Sep. 13, 2005 (5 pages).
Response to Written Opinion; International Application No. PCT/FI2006/000303; Jul. 16, 2007 (8 pages).
International Preliminary Report on Patentability; International Application No. PCT/FI2006/000303; International Filing Date Sep. 13, 2006 (8 pages).
Communication Under Rule 71(3) EPC; Application No. 06 778 512.1-1211; Jan. 18, 2010 (4 pages).
International Search Report; International Application No. PCT/FI2006/000303; Date of Completion of the International Search Apr. 13, 2007; Date of mailing of the International search report Apr. 19, 2007 (2 pages).
Finnish Search Report FI20050913; Jul. 11, 2006 (1 page).
O. D. Shapilov and Ya. L. Kostyukovskii in Kinetika Kataliz, "Reaction Kinetics of Hydrogen Peroxide with Formic Acid in Aqueous Solutions", vol. 15, No. 4, 1974, pp. 1065-1067 (Supplied by the British Library, UDC 547.661.729, pp. 947-948).
Jones, C. W., "Activation of Hydrogen Peroxide in the Peroxide in the Presence of Organic Compounds", Royal Society of Chemistry; clean Technology Monographs, 1999, pp. 61-77.
Mosovsky et al. in Collect. Czech. Chem. Commun., "Kinetics of Formation of Peroxyformic Acid", vol. 61, 1996, pp. 1457-1463.
Merka et al., "Antifungal Properties of Performic and Perpropionic Acids", Journal of Hygiene, Epidemiology, Microbiology and Immunology, 1968, vol. 12, pp. 115-121.
"Concentrated Hydrogen Peroxide: Summary of Research Data on Safety Limitations" (Shell Chemical Company Bulletin, 1961).

* cited by examiner

*Primary Examiner* — Paul Zarek
(74) *Attorney, Agent, or Firm* — Thomas Horstemeyer, LLP

(57) ABSTRACT

The present invention relates to a process for the preparation of a solution comprising a first peroxy acid comprising performic acid and a second peroxy acid, said process comprising forming a carboxylic acid solution comprising a first carboxylic acid comprising formic acid, a second carboxylic acid and hydrogen peroxide, wherein the amount of formic acid is from 0.5 to 20% by weight of the amount of the second carboxylic acid, and allowing the components to react to form a solution comprising performic acid and said second peroxy acid, the amount of peroxy acids being at least 5% by weight. The invention also relates to a storable solution comprising performic acid and said second peroxy acid. The solution can be used as a disinfecting agent for controlling micro-organisms.

7 Claims, No Drawings

PROCESS FOR THE PREPARATION OF PEROXY ACIDS

FIELD OF THE INVENTION

The invention relates to the preparation of relatively concentrated, storable peroxy acid solutions containing performic acid. The invention also relates to relatively concentrated, storable peroxy acid solutions and to the use of such solutions.

BACKGROUND OF THE INVENTION

Hydrogen peroxide is known as a moderately effective disinfecting agent with some bacteriostatic properties. It is applied in the disinfection of sewage waters etc. The utilization of the reactivity of hydrogen peroxide with metal ions (Fenton reaction) is the most powerful use of hydrogen peroxide in disinfection. UV irradiation is another applicable way to activate hydrogen peroxide in disinfection. Both Fenton reaction and UV irradiation produce hydroxyl radicals to the reaction media. However, the disinfection power of hydrogen peroxide is not sufficient for most of the microbes.

Peracetic acid (PAA) is known as an effective disinfecting agent providing a rapid reduction of bacteria growth for most of the common bacteria. It is applied in the sterilization of the equipment in dairy industry. Moreover, PAA is applied in pulp and paper industry for the control of the microbial growth in process waters. In addition, peracetic acid is applied in the post-bleaching of kraft pulps after delignification and peroxide bleaching steps.

Peracetic acid is traditionally prepared via an equilibrium reaction between acetic acid and hydrogen peroxide resulting in an equilibrium solution:

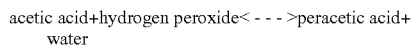

This reaction occurs only when catalyzed by a strong mineral acid, e.g. sulfuric acid.

The equilibrium solution of peracetic acid is used as a disinfecting agent for example in process water applications, greenhouses, dairy industry etc.

Similar equilibria occur with formic acid and hydrogen peroxide, resulting in solutions containing performic acid (PFA). PFA solutions are proven to be more effective disinfecting agents than peracetic acid solutions. Due to instability and high reactivity of PFA the solutions of PFA are not stable. Thus, PFA solutions have to be prepared in situ. A stable disinfecting agent comparable with PFA should be desirable for applications in greenhouses, industrial and institutional (I&I) cleaning and control of microbial growth in process waters e.g. in pulp and paper (P&P) industry.

In WO 94/20424 performic acid is successfully applied in the control of microbial growth in the horticulture. A dilute performic acid solution fed into the nutrient solution or drain water prevents the growth of algae in the pipelines going to the plants preventing them from plugging. Extensive studies of the applicant have shown that the equilibrium mixtures of PAA are not applicable in such applications due to their lower reactivity towards microbes. Furthermore, the disinfection power of formic acid in the absence of hydrogen peroxide is proven to be negligible compared to peroxy acids.

The stability of peroxy acids is known to increase with increasing molecular weight. On the other hand, together with the reactivity, the disinfection power of peroxy acids increases with the decrease of the molecular weight. Performic acid (PFA) is known as the most powerful disinfection agent among the peroxy acids. Several studies have shown the effect of performic acid in the control of microbial growth. One of the earlier references is J. Hyg. Epidem. Microbiol. Immunol. (1968) 12, 115.

WO 94/20424 describes the preparation of performic acid solutions in situ by reacting formic acid and hydrogen peroxide in a molar ratio of from 1:10 to 10:1, preferably from 1:1 to 1:5. The PFA solution can be employed for preventing and combating harmful microorganisms. Typically PFA is used in an amount of 1-1000 ppm.

EP 231632 A discloses the industrial use of performic acid as a sanitizer. The performic acid solution is prepared in situ from an aqueous solution containing from 10 to 50% by weight hydrogen peroxide and a solution containing from 5 to 100% by weight formic acid by reacting the same in the presence of a catalyst, the weight ratio of hydrogen peroxide to formic acid being in the range of from 1:6 to 1:1.5.

For greenhouse disinfection purposes, the solution of PFA is prepared by mixing for example, 35% hydrogen peroxide with 15% formic acid solution. The resulting solution is then diluted with the nutrient solution and fed to the plants.

Due to the fact that performic acid solutions are explosive in higher concentrations, only low concentrations of performic acid solutions can be handled safely.

Mixtures of dilute solutions of performic acid and peracetic acid are known from the recent patent literature.

U.S. Pat. No. 6,211,237 B1 discloses a dilute disinfecting agent comprising small amounts of performic acid and peracetic acid, the total amount of these peracids typically being less than 4% by weight. The main component of the agent is hydrogen peroxide, the amount thereof typically being about 50% by weight. The agent may be used for example for disinfecting swimming pool waters. The dilute solutions of PFA and PAA with hydrogen peroxide are prepared in situ. It is also known for the man skilled in the art that peroxy acid solutions, even the equilibrium solutions of performic acid, are relatively stable at low concentrations, up to 2% by weight, for several days.

US 2004/0035537 describes a method for bleaching pulp with a solution containing peracetic acid and performic acid. Also in this application, dilute peroxy acid solutions are prepared in situ by bringing acetic acid and formic acid into contact with hydrogen peroxide at a concentration greater than 50% by weight. The ratio of acetic acid+peracetic acid to formic acid+performic acid is preferably 9 to 1 by volume. The amount of peracids in the obtained solution is very low, typically less than 2% by weight.

U.S. Pat. No. 6,284,793 B1 discloses a biocidal agent for treating ballast sea water. The biocidal agent is in the form of a solution containing peracetic acid, performic acid, acetic acid, formic acid, hydrogen peroxide and water and optionally a mineral acid catalyst and active oxygen stabilizers. Such a solution may be obtained by adding formic acid to an equilibrium peracetic acid solution, typically containing 1 to 15% by weight peracetic acid. According to this document performic acid is more effective compared with peracetic acid, but also more susceptible to decomposition and therefore formic acid is added to the solution containing peracetic acid only just prior to use. When the equilibrium peracetic acid and formic acid are used in combination, the formic acid being added directly to the peracetic acid or simultaneously to the ballast water, the formic acid is used in a quantity of 10 to 1000% by weight, based on the sum of peracetic acid and acetic acid. In the working examples the formic acid is added to equilibrium peracetic acid in an amount of about 800% by weight, based on the sum of peracetic acid and acetic acid.

Peroxy acid solutions are most commonly prepared via an equilibrium reaction of hydrogen peroxide with the appropriate carboxylic acid. In the case of peracetic acid and carboxylic acids having higher molecular weight, an acid catalysis is required in order to reach the equilibrium in an appropriate period of time. Mineral acids, for example sulphuric acid, hydrochloric acid etc. are commonly applied as acid catalysts in such reactions. In the case of formic acid, an additional acid catalyst is not necessary according to the literature (Jones, C. W., "Applications of hydrogen peroxide and derivatives", Royal Society of Chemistry; Clean Technology Monographs, 1999, pp. 61-77).

DESCRIPTION OF THE INVENTION

According to the invention it was surprisingly found that in equilibrium solutions prepared by mixing acetic acid and hydrogen peroxide in molar ratios in the range from 0.5:1 to 8:1 (mol acetic acid/mol hydrogen peroxide), acetic acid can be replaced by formic acid in an amount of up to 20% by weight, and yet provide a storable solution. In the presence of common peroxide stabilizers, such concentrated peroxy acid solutions are stable enough for the storage for several weeks. According to the invention it was found that substantial amounts of formic acid can be introduced without loosing the stability of the resulting peroxy acid solution.

Thus, in one aspect of the invention there is provided a process for the preparation of a solution comprising a first peroxy acid comprising performic acid and a second peroxy acid, said process comprising forming a carboxylic acid solution comprising a first carboxylic acid comprising formic acid, a second carboxylic acid and hydrogen peroxide, wherein the amount of formic acid is from 0.5 to 20% by weight of the amount of the second carboxylic acid, and allowing the components to react to form a solution comprising performic acid and said second peroxy acid, the amount of peroxy acids being at least 5% by weight.

The peroxy acid solution can be prepared by pre-mixing the first and second carboxylic acids followed by the addition of a hydrogen peroxide solution. Alternatively, the peroxy acid solution can be prepared by mixing an aqueous solution of the second carboxylic acid, e.g. acetic acid solution, and hydrogen peroxide solution followed by the addition of the first carboxylic acid, i.e. formic acid to the equilibrium mixture. The reaction equilibria are set in 1-2 hour or in a longer period of time, largely depending on the temperature of the reaction mixture. The reaction temperature can be in the limits of 0° C. to 80° C. Preferably, the reaction temperature should be between 0° C. and 50° C. Most preferably, the reaction temperature should be between 0° and 25° C. in order to obtain the best stability of the peroxy acid solution.

The concentrations of the carboxylic acid solutions applied in the formation of the peroxy acid solution can vary from 30% to 100% by weight. Generally, higher concentrations are favorable in order to reach higher final concentrations of the peroxy acids.

The concentration of hydrogen peroxide solution used for the formation of peroxy acid solution can be between 10% and 80% by weight. The hydrogen peroxide is introduced into the solution as an aqueous hydrogen peroxide solution, preferably having a concentration of 10% to 55%, more preferably 30% to 55% by weight. Generally, higher concentrations of hydrogen peroxide are favorable in order to reach higher final concentrations of the peroxy acids. However, safety aspects must be taken into consideration in the preparation of concentrated peroxy acid solutions. The principles of the safety aspects concerning the preparation of mixtures of hydrogen peroxide and organic matter is described for example in "*Concentrated Hydrogen Peroxide: Summary of Research Data and Safety Limitations*" (Shell Chemical Corp., Bull. SC 59-44).

The reaction time is largely depending on the carboxylic acids used. The kinetics of the formation of peroxyformic acid is described by Mosovsky et al. in *Collect Czech. Chem. Commun*. vol 61, 1996, pp. 1457-1463 and by O. D. Shapilov and Ua. L. Kostyukovskii in *Kinetika Kataliz* vol. 15, n:o 4, 1974 p. 1065. The kinetics of the formation of peracetic acid is also well known in the literature. However, the kinetics of the formation of the mixtures of the peroxy acids may be different when mixtures of carboxylic acids are applied.

The amount of peroxy acids in the obtained solution is preferably from 5 to 20% by weight, more preferably from 10 to 20% by weight.

The amount of formic acid is preferably from 2 to 15% by weight of the amount of the second carboxylic acid.

The molar ratio of the carboxylic acids to hydrogen peroxide in the carboxylic acid solution is preferably in the range from 0.5:1 to 8:1, more preferably from 0.7:1 to 2:1. Said molar ratio may also be in the range from 2:1 to 8:1.

The obtained solution is preferably an equilibrium solution additionally comprising formic acid, the second carboxylic acid and hydrogen peroxide.

The amount of formic acid and performic acid in the equilibrium solution is preferably from 2 to 20% by weight.

Said second carboxylic acid is preferably an aliphatic $C_2$-$C_{18}$ carboxylic acid including acetic acid, propionic acid, phtalic acid, oxalic acid, malic acid, maleic acid and fumaric acid and mixtures thereof, and said second peroxy acid is preferably an aliphatic $C_2$-$C_{18}$ peroxy carboxylic acid including peracetic acid, perpropionic acid, peroxy phtalic acid, peroxy oxalic acid, peroxy malic acid, peroxy maleic acid and peroxy fumaric acid and mixtures thereof. Especially preferred are acetic acid and peracetic acid.

The formation of the equilibrium mixtures of peroxy acids can be catalyzed by the addition of strong acids. The strong acids can be organic acids. Preferably, low molecular weight carboxylic acids can be used as reaction catalysts. Most preferably, formic acid can be used as a catalyst.

Alternatively, the formation of the equilibrium mixtures of peroxy acids can be catalyzed by mineral acids. The mineral acids applicable for catalyzing the formation of peroxy acids include sulphuric acid, phosphoric acid, hydrochloric acid, pyrophosphoric acid and polyphosphoric acid and mixtures thereof. One advantage of for example a sulphuric acid catalyst is that it also forms a peroxy acid (Caron acid) to some extend.

The amount of the acid catalyst can be from 0.1 to 20% of the weight of the solution, more preferably from 1 to 10% of the weight of the solution, most preferably from 1 to 5% of the weight of the solution.

In addition, ion exchange resins in their acidic forms can be used as a catalyst of said reaction.

Additionally, conventional additives may be introduced into the solution. The additives include stabilizers such as phosphonates, e.g. 1-hydroxy ethylene-1,1-diphosphonic acid (HEDPA), and pyridinecarboxylic acids, e.g. dipicolinic acid, chelating agents and radical scavengers. Also mixtures of stabilizers may be employed. The amount of stabilizer(s) may be from 0.01 to 1% by weight, preferably from 0.05 to 0.5% by weight.

In a second aspect of the invention there is provided a storable solution comprising a first peroxy acid comprising performic acid, a second peroxy acid, a first carboxylic acid comprising formic acid, a second carboxylic acid and hydrogen peroxide, the amount of formic acid and performic acid being from 0.5 to 20% by weight of the total amount of the second carboxylic acid and the second peroxy acid, and the amount of peroxy acids being at least 5% by weight.

In this specification the term "storable" means that the decrease of active oxygen (peroxy acids+hydrogen peroxide) in the peroxy acid solution is less than 20% by mol after 7 days' storage at room temperature. The decrease is preferably less than 15% by mol, and more preferably less than 10% by mol.

The amount of peroxy acids in the solution is preferably from 5 to 20% by weight, more preferably from 10 to 20% by weight.

The molar ratio of the peroxy acids and carboxylic acids to hydrogen peroxide in the solution is preferably in the range from 0.5:1 to 8:1, more preferably from 0.7:1 to 2:1. Said molar ratio may also be in the range from 2:1 to 8:1.

The solution is preferably an equilibrium solution.

The amount of formic acid and performic acid in the solution is preferably from 2 to 20% by weight.

Said second carboxylic acid and said second peroxy acid are as defined above.

Preferably the solution additionally comprises a stabilizer as defined above.

The invention also relates to the use of the solution as defined above as a disinfecting agent for controlling microorganisms. The solution of the invention may be used as a disinfecting agent for example in process water applications, greenhouses, dairy industry, I&I cleaning, P&P industry, for example for controlling microbial growth on paper machines etc. The peroxy acid solution may also be used as bleaching agent in pulp bleaching wherein it can be used e.g. as a post-bleaching agent of residual lignin. Additionally, the peroxy acid solution is an effective impregnating agent of wood chips before the preparation of mechanical pulp.

Concentrated solutions of performic acid and peracetic acid according to the invention have superior effectiveness in the control of microbial growth in process waters, greenhouse nutrient solutions, disinfection of sewage waters etc. compared to pure peracetic acid solutions.

Moreover, these PFA/PAA solutions can be prepared and stored for several weeks without remarkable decomposition. As the anti-microbial features of the said solutions are equal to performic acid solutions, the use of PFA/PAA solutions provides a safe alternative for the use of performic acid solutions.

This is a remarkable advantage, since performic acid solutions are not storable and thus, they have to be prepared in situ prior to use. Another advantage compared to performic acid solutions is the improved safety factor. PFA/PAA solutions are comparable to pure PAA solution in terms of safety aspects.

The good stability of the PFA/PAA solutions of the present invention was surprising, since performic acid solutions at higher concentrations are regarded to be unstable.

Compared to the use of performic acid, these solutions of PAA and PFA provide a good alternative also in terms of corrosivity. By applying a mixture of PAA and PFA having the similar anti-microbial features as performic acid, the risk of the corrosion of the equipment is remarkably lower.

As explained above up to 20% by weight, preferably up to 15% by weight of peracetic acid or another peroxy acid can be replaced by performic acid, still providing storable solutions. Following advantages can be obtained by the present invention:

Firstly, a substantial amount of performic acid is formed into the solution and this should increase the disinfecting power of the peroxy acid solution. Secondly, peroxy acid solutions, suitable for greenhouse applications etc can be prepared and stored, whereas nowadays PFA solutions must be prepared in situ from the solutions of formic acid and hydrogen peroxide. Thirdly, the resulting peroxy acid solution could be used as bleaching agent in pulp bleaching wherein it can be used e.g. as a post-bleaching agent of residual lignin. Additionally, the peroxy acid mixture is an effective impregnating agent of wood chips before the preparation of mechanical pulp.

In this specification percentages refer to % by weight unless otherwise specified. The invention is explained in more detail in the following examples.

Example 1

0.6%, 3.04%, 4.99%, 10.04% and 15.01% solutions of formic acid (FA) in acetic acid (AA) were prepared. The solutions were mixed in molar ratio 2:1 (AA/$H_2O_2$) with 50.5% $H_2O_2$. As stabilizers, phosphonate HEDPA, 500 mg/l) and dipicolinic acid (DPA, 300 mg/l) were added into each solution. The resulting solutions were stirred overnight at room temperature. The solutions were stored in dark, at RT for 7 days and the concentrations of peroxy acid (here calculated as peracetic acid) and hydrogen peroxide were determined by titrations. After 3 d storage, 0.48% of sulfuric acid was added to further catalyze the reaction. The total active oxygen content (peracid+peroxide) was determined for each sample. The test results are shown in following Tables 1 to 3. The stability % describes the ratio between the analyzed amount of peracid (mol/kg)+$H_2O_2$ (mol/kg) and the originally added $H_2O_2$ (mol/kg).

TABLE 1

(results after 1 day)

| % of FA in AA | $H_2O_2$ g/kg | $H_2O_2$ mol/kg | peracid g/kg | peracid mol/kg | act (O) mol/kg | stability % |
|---|---|---|---|---|---|---|
| 0.60 | 141.18 | 4.15 | 87.34 | 1.12 | 5.27 | 100.59% |
| 3.04 | 129.06 | 3.80 | 101.29 | 1.30 | 5.09 | 97.33% |
| 4.99 | 129.74 | 3.82 | 103.64 | 1.33 | 5.14 | 97.61% |
| 10.04 | 117.09 | 3.44 | 113.88 | 1.46 | 4.90 | 93.32% |
| 15.01 | 110.41 | 3.25 | 117.73 | 1.51 | 4.76 | 90.65% |

TABLE 2

(results after 3 days)

| % of FA in AA | $H_2O_2$ g/kg | $H_2O_2$ mol/kg | peracid g/kg | peracid mol/kg | act (O) mol/kg | stability % |
|---|---|---|---|---|---|---|
| 0.60 | 122.27 | 3.60 | 123.16 | 1.58 | 5.18 | 99.36% |
| 3.04 | 112.31 | 3.30 | 135.52 | 1.74 | 5.04 | 96.16% |
| 4.99 | 111.32 | 3.27 | 131.05 | 1.68 | 4.95 | 94.64% |
| 10.04 | 99.34 | 2.92 | 137.37 | 1.76 | 4.68 | 89.46% |
| 15.01 | 89.29 | 2.63 | 136.67 | 1.75 | 4.38 | 84.67% |

TABLE 3

(results after 7 days)

| % of FA in AA | $H_2O_2$ g/kg | $H_2O_2$ mol/kg | peracid g/kg | peracid mol/kg | act (O) mol/kg | stability % |
|---|---|---|---|---|---|---|
| 0.60 | 68.18 | 2.01 | 241.53 | 3.10 | 5.10 | 98.06% |
| 3.04 | 68.66 | 2.02 | 233.59 | 2.99 | 5.01 | 94.89% |
| 4.99 | 67.66 | 1.99 | 224.47 | 2.88 | 4.87 | 92.90% |

TABLE 3-continued (results after 7 days)

| % of FA in AA | H$_2$O$_2$ g/kg | H$_2$O$_2$ mol/kg | peracid g/kg | peracid mol/kg | act (O) mol/kg | stability % |
|---|---|---|---|---|---|---|
| 10.04 | 64.33 | 1.89 | 204.29 | 2.62 | 4.51 | 86.64% |
| 15.01 | 62.55 | 1.84 | 191.27 | 2.45 | 4.29 | 82.01% |

From the tables 1 to 3 can be seen the amounts and formation rates of peracids when different amounts of acetic acid are replaced by formic acid. The decrease of active oxygen (peracid+peroxide) indicates the decomposition of total peroxy acids when the amount of formic acid is increased in the starting solution. However, even when 15% of acetic acid was substituted by formic acid, over 80% of the active oxygen was preserved after 7 days' storage.

Example 2

Efficacy of PFA-PAA Mixtures Towards Pre-Grown Biofilm on Stainless Steel Surface Kemira has developed a new test intended for rapid efficacy testing of anti-biofilm agents. The test is disclosed in patent application WO 2005/045132. In this assay different products are compared for their relative efficacy in inactivation/removal of pre-grown biofilms. The real situation in paper machines is often that it is not enough to prevent formation of new biofilms, but the anti-biofilm agents should also perform on pre-contaminated surfaces. In the new test pre-grown biofilms are exposed for a short time, and after that the viability of remaining biofilms is quantified.

Biofilms were produced on the surfaces of stainless steel protrusions. This was achieved by immersing the steel plate with protrusions to a mixture of true primary-biofilm formers of paper industry (*Deinococcus geothermalis*, *Pseudoxanthomonas taiwanensis* and *Meiothermus silvanus*) mixed with clear filtrate from a neutral board machine and cultivating in continuous shaking (2 d, 45° C.).

Grown-up biofilms on the protrusions were exposed to different biocides for 1.5 hour at room temperature. The viability of remaining biofilms was measured by transferring the stainless steel plates to sterile R2 broth and incubating at 45° C. for 21 h. The amount of new biofilm formed indicated the survival rate of the original, treated biofilms. The tested biocides were:

PFA-PAA: a mixture of performic acid and peracetic acid was prepared by mixing 5.9 g formic acid solution (concentration 75 weight %) to 44.6 g acetic acid solution (concentration 99 weight %) and 100 g hydrogen peroxide solution (concentration 50 weight %) was added to the carboxylic acid mixture by cooling. Additionally 2.0 g stabilizer and 7.5 g concentrated sulphuric acid was added. The peroxy acid content was 9.3 weight % and H$_2$O$_2$ content 28 weight %.

ePAA: an equilibrium peracetic acid solution trade name Kemirox WT, containing 15 weight % of pure peracetic acid, 15 weight % hydrogen peroxide and 24 weight % acetic acid.

The dosing of the mixture was based on the sum of peracids. Following doses were used 0, 2, 3, 4, 5, 6, 7½, 10 and 15 ppm of PAA or a mixture of PAA and PFA, respectively. All biocides were treated as active ingredient and weighted in deionized water and diluted in tap water.

The test results show that the PFA-PAA mixture was a clearly better biocide than ePAA. A clear effect was observed with 3 ppm and a complete inactivation with 5 ppm. When an ordinary ePAA solution was applied a clear effect was not seen until 10 ppm concentration of PAA was applied. Even 15 ppm concentration of ePAA did not result in complete inactivation of the microbes. Based on the active PAA content, PFA-PAA mixture was 3 to 4 times more efficient than ePAA. As product, PFA-PAA was roughly two times more efficient than ePAA in biofilm inactivation.

The invention claimed is:

1. A storable solution comprising a first peroxy acid comprising performic acid, a second peroxy acid, a first carboxylic acid comprising formic acid, a second carboxylic acid comprising acetic acid, hydrogen peroxide, and a stabilizer, the total amount of formic acid and performic acid being from 0.5 to 20% by weight of the total amount of the second carboxylic acid and the second peroxy acid, the molar ratio of the peroxy acids and carboxylic acids to hydrogen peroxide being 2:1 to 8:1, and the total amount of peroxy acids being at least 5% by weight.

2. The solution according to claim 1 wherein the total amount of peroxy acids in the solution is from 5 to 20% by weight.

3. The solution according to claim 1 wherein the molar ratio of the peroxy acids and carboxylic acids to hydrogen peroxide is 0.7:1 to 2:1.

4. The solution according to claim 1 wherein the solution is an equilibrium solution.

5. The solution according to claim 1 wherein the total amount of formic acid and performic acid in the solution is from 2 to 20% by weight.

6. The solution according to claim 1, wherein the stabilizer comprises a phosphonate, a pyridinecarboxylic acid, or a mixture thereof.

7. The solution according to claim 1,
   wherein the second carboxylic acid is acetic acid;
   wherein the total amount of peroxy acids is from 5 to 20% by weight; and
   wherein the carboxylic acid solution further comprises a stabilizer selected from the group consisting of 1-hydroxyethylene-1,1-diphosphonic acid, dipicolinic acid, and mixtures thereof.

* * * * *